(12) United States Patent
Todosiev et al.

(10) Patent No.: US 6,494,500 B1
(45) Date of Patent: Dec. 17, 2002

(54) UNIVERSAL HIGH PRESSURE LIQUID CONNECTOR

(76) Inventors: Geoff Todosiev, c/o Isolation Technologies, Inc., 4 Business Way, Hopedale, MA (US) 01747; Michael Rigoli, c/o Isolation Technologies, Inc., 4 Business Way, Hopedale, MA (US) 01747

(*) Notice: Subject to any disclaimer, the term of this patent is extended or adjusted under 35 U.S.C. 154(b) by 0 days.

(21) Appl. No.: 09/570,307

(22) Filed: May 12, 2000

Related U.S. Application Data

(60) Provisional application No. 60/134,015, filed on May 12, 1999.

(51) Int. Cl.[7] .................................................. F16L 25/00
(52) U.S. Cl. ........................................ 285/342; 285/279
(58) Field of Search .................................. 285/354, 279

(56) References Cited

U.S. PATENT DOCUMENTS

| | | |
|---|---|---|
| 4,732,672 A | 3/1988 | Kiang et al. |
| 5,163,722 A * | 11/1992 | Worden .................. 285/279 X |
| 5,234,235 A * | 8/1993 | Worden .................. 285/353 X |
| 6,193,286 B1 * | 2/2001 | Jones et al. ................. 285/354 |

* cited by examiner

*Primary Examiner*—Lynne H. Browne
*Assistant Examiner*—John R. Cottingham
(74) *Attorney, Agent, or Firm*—Lambert & Associates; Gary E. Lambert, Esq.; Edward Timmer

(57) ABSTRACT

The present invention is a universal self-adjusting high pressure liquid connector for use with high pressure liquid chromatography (HPLC) columns requiring liquid-tight and leak free seals between fittings and unions. The present apparatus provides a liquid-tight seal between the end of a HPLC end fitting and a end cap thereby eliminating any potential dead volume in the area of the connection. The apparatus comprises a body, a fixed ferrule, a replaceable ferrule, a stem disposed in the body and a biasing spring slidingly mounted on a capillary tube of that extends through the connector. The spring biases the capillary tube of the connector into the HPLC end fitting, self-adjusting and maintaining a pressure sufficient to ensure a liquid-tight seal notwithstanding the depth of the HPLC tube stop or ferrule stop of the mating HPLC column.

12 Claims, 5 Drawing Sheets

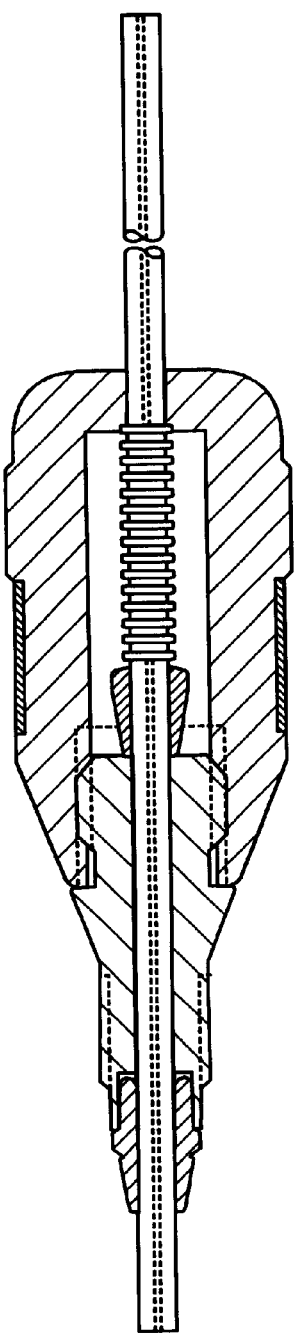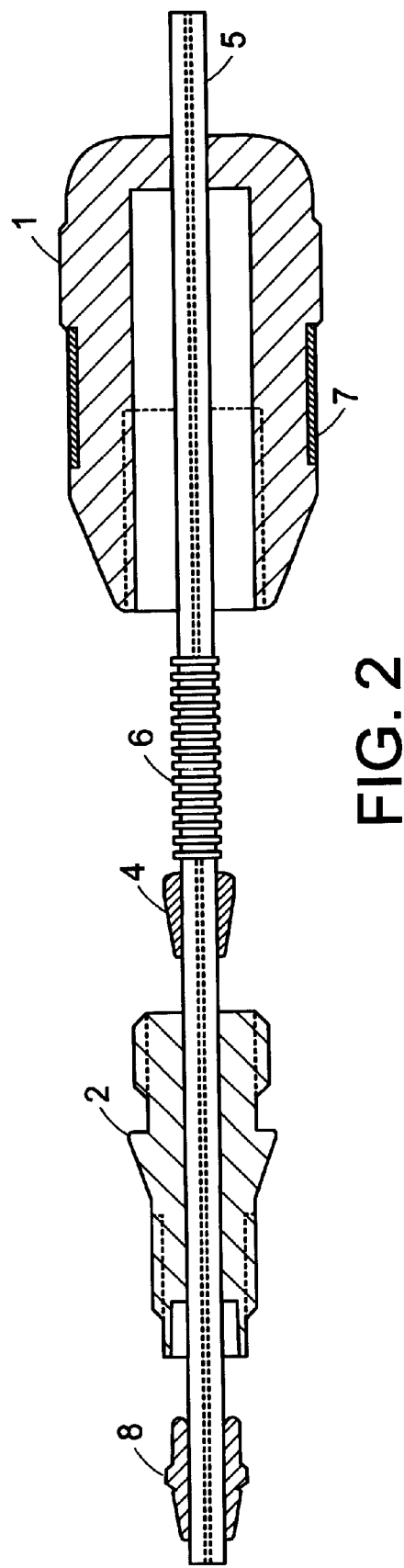
FIG. 1
FIG. 2

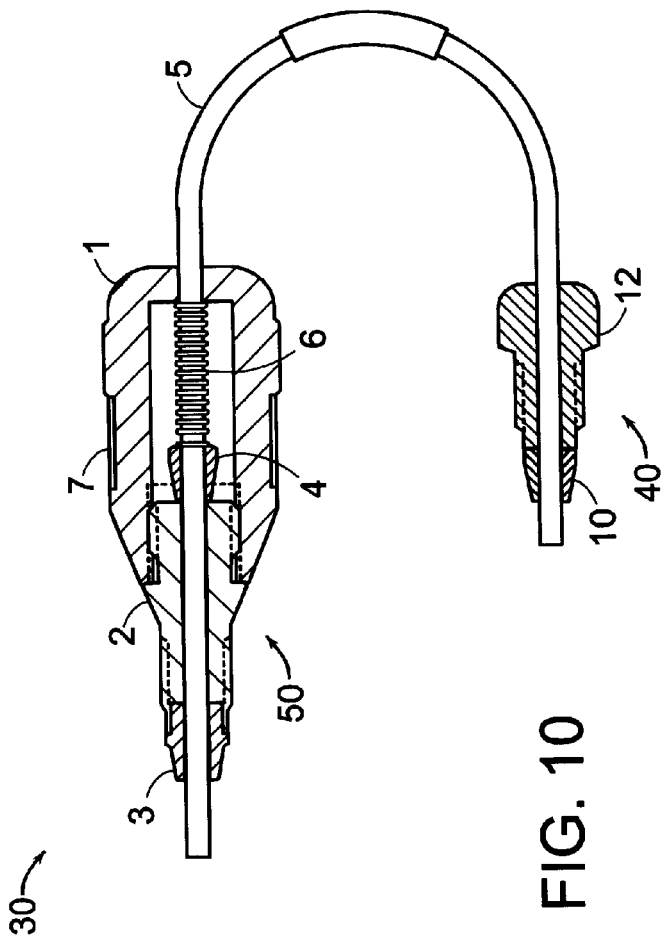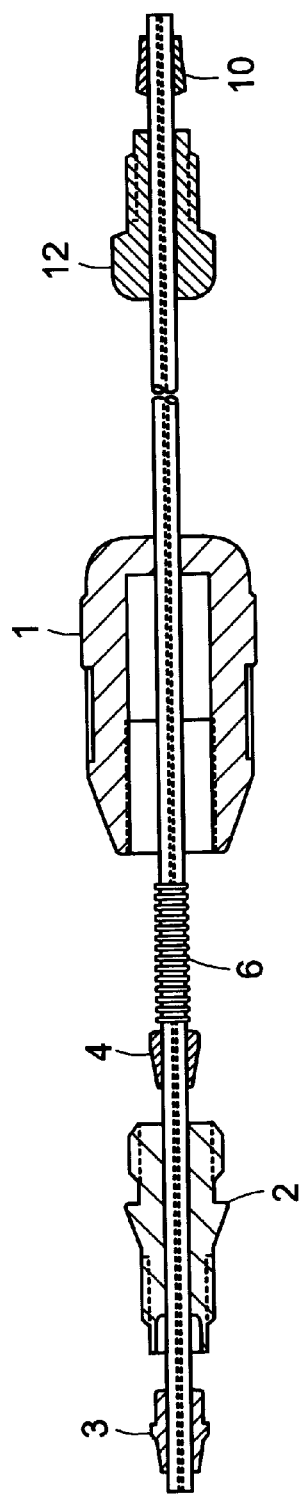
FIG. 10
FIG. 11

UNIVERSAL HIGH PRESSURE LIQUID CONNECTOR

CROSS REFERENCE TO RELATED APPLICATIONS

This application claims the benefit of Provisional Application, Ser. No. 60/134,015 filed May 12, 1999 by the same inventors.

BACKGROUND OF THE INVENTION

This invention relates generally to improvements in the field of high pressure liquid connectors and more specifically to high pressure liquid connectors for use in high pressure liquid chromatography (HPLC) applications.

HPLC columns are produced by a number of different manufacturers. While there are some standard design considerations, HPLC manufacturers employ unique design specifications and techniques resulting in HPLC columns having proprietary parts. Of particular interest in the present invention are the proprietary end fittings of HPLC columns. Each of the columns utilizes an end fitting or end cap. The proprietary end fittings have different ferrule and tube stop lengths. Since each manufacturer uses proprietary end fittings there exists the problem that between the end fitting and the portion of the column containing the filter bed a dead volume can exist. The dead volume refers to the liquid space between the end of the liquid input line and the portion of the column containing the filter bed. Any amount of dead volume reduces the effectiveness of the column, wastes a portion of the liquid sample and could even be hazardous if this dead volume of liquid is spilled when the column is removed from the system or otherwise opened. To eliminate the dead volume, tubing is provided. The tubing provides a path through which the sample is made to flow. The tubing is made to intimately contact an inlet and outlet portion of the column containing the filter bed in a liquid-tight fitting, thereby hopefully eliminating any dead space where liquid can collect. The difficulty associated with trying to eliminate or at least reduce the dead volume in this manner is that each proprietary column requires a different length of tubing in order to bottom out against the column end due to the different ferrule and tubing stop lengths.

As the column is assembled, the tubing of a connector is pushed into the end fitting as far as possible thereby contacting the column end. Technicians and others assembling HPLC columns must individually gauge how far to insert the end cap connector tubing into the HPLC column end fitting. Oftentimes the tubing is crimped or otherwise distorted when the end cap connector is fully tightened. This compromises the tubing and leads to accumulation of fluid or malfunctioning of the column instead of eliminating a dead volume as desired.

SUMMARY OF THE INVENTION

The apparatus of the present invention is a universal high pressure liquid connector, which automatically accommodates differing ferrule depths, and tube stops of proprietary HPLC column end fittings thereby reducing and eliminating the potential dead volume and or leaks in mating connections. The present invention employs an internal spring-loaded mechanism that maintains sufficient pressure in the critical area of the connection once the universal high pressure liquid connector of the present invention and the HPLC column fitting have engaged. The critical area of the connection being where the end of the universal high pressure liquid connector mating tubing bottoms out on the internal female fitting and the ferrule of the mating connection seats within the geometry of the mating port connection of the HPLC column. If an incorrect connection is made, i.e. the tubing does not bottom out, and or the ferrule seats improperly, a dead volume is created resulting in poor chromatographic performance or a leak path is created.

It is therefore an objective of the present invention to provide a high pressure liquid connector for use in HPLC columns having universal compatibility. Since there are a variety of industry standard port depths relating to HPLC column female fitting geometry, the apparatus of the present invention is designed to accommodate all port depths. Similar to a finger-tight fitting, the apparatus of the present invention does not have a fixed ferrule. Instead, the ferrule has the ability to freely slide up and down the connecting tubing, allowing the apparatus of the present invention to adjust to any port depth. Unlike finger tight fittings however, one using the present invention does not have to maintain pressure on the tubing to ensure a zero dead volume connection. The internal spring-loaded mechanism ensures the zero dead volume connection by maintaining pressure on the tubing into the bottom of the female port. Therefore, regardless of the port depth, the universal high pressure liquid connector of the present invention will always guarantee a zero dead volume connection.

Furthermore, the apparatus of the present invention requires no wrenches or other special tools to make a liquid-tight sealed connection with a HPLC column end fitting. It is important to note that the present invention is stable to 6000 pounds per square inch (psi).

The sliding ferrule-to-capillary tube configuration of the present invention is better than previous connectors having fixed ferrule fitting configurations in a number of ways. First, fixed ferrule fittings are not universal. Normally, once the ferrule has been swaged to the capillary tube in a fixed ferrule connector apparatus, the connector can only be used with a female fitting having an exact matching port depth. Furthermore, it has been observed that female port depths vary even within the same batch of fittings from the same supplier alleging to be made to the same specifications. Therefore, unless a connector having a fixed ferrule fitting is swaged when changing connections from one fitting to the next, a zero dead volume and leak free connection cannot be guaranteed.

Secondly, connectors having fixed ferrule fittings typically require wrenches to make the connection. The universal high pressure liquid connector of the present invention incorporates a finger tight engagement means, which does not require the use of wrenches or other tools in order to effectuate a leak proof mating connection.

Thirdly, the fixed ferrule fittings of previous designs can deform the connecting tubing. By overswaging the fitting onto the capillary tubing, the tubing may be crimped, thereby causing a deformity on the inner wall of the connector capillary tubing, which can lead to poor chromatographic performance.

The apparatus of the present invention is better than traditional finger tight fittings in a number of aspects. First, traditional finger tight fittings require the technician to maintain pressure on the tubing into the female port to ensure a zero dead volume connection. Operator error and or ignorance may, and does, lead to improper connection techniques wherein the end of the capillary tube of the connector does not properly bottom out on the mating female fitting, thus introducing a dead volume and potential leakpaths. The apparatus of the present invention however applies constant pressure on the connector tubing inserted into the female port via the internal spring-loaded mechanism, thereby greatly reducing the potential for operator error.

Secondly, since a technician must maintain pressure on the tubing while making a connection, and different technicians use different hand positions to do so, the connector tubing may become bent in many ways. When the tubing becomes bent in the last 1–2 centimeters where the finger-tight fitting is located, a leak may occur, thus rendering the tubing useless and requiring replacement of the capillary tubing and possibly the finger tight fitting as well since the bent capillary tubing may have deformed the finger tight fitting.

Thirdly, most finger tight fittings use a polymeric male thread that degrades after repeated connections. The male polymeric threads will degrade to a point where they will no longer ensure a positive connection thus rendering the finger tight fitting no longer useable. The finger tight connection then requires replacement. The preferred embodiment of the present universal self-adjusting high pressure liquid connector typically has a stainless steel male thread sold under the name of NITRONIC-60 located on the exterior of the connector's stem for threadedly engaging with a HPLC column. Yet another version of the present invention would further comprise male threads constructed of an anti-gall material by Carpenter Technology, Inc under the name of GALL-TOUGH. However any other material with similar properties that will not degrade and will not gall due to its metallurgic properties is appropriate and contemplated within the scope of the present invention.

The present invention offers additional benefits not realized from using traditional stainless steel finger tight fittings. Traditional adjustable stainless steel fittings require the technician to maintain pressure on the tubing into the female port to ensure a zero dead volume connection. Additionally, these stainless fittings require the technician to push the ferrule up the tubing to expose enough tubing beyond the ferrule to ensure a zero dead volume connection each time the traditional adjustable connector is used. The universal self-adjusting high pressure liquid connector of the present invention however applies a self-adjusting pressure on the capillary tubing inserted into the female port via the internal spring-loaded mechanism each time the universal self-adjusting high pressure liquid connector is used.

Secondly, most traditional adjustable stainless fittings use a stainless steel male thread, which after repeated connections will degrade. The stainless steel threads will degrade to a point where they will have a tendency to gall and will no longer be useable requiring replacement. The universal self-adjusting high pressure liquid connector, as discussed above, typically has a stainless steel male thread that will not degrade and will not gall due to its metallurgic properties.

Other design applications for the present invention include the incorporation of the connection device into a hand tight cartridge style column and guard column system. The Isolation Technologies, Inc. product known under the trademark QUICKSEAL analytical cartridge system is being modified to include the apparatus connector at the inlet and outlet ends of columns as short as 1 cm in length with no restrictions on column lengths. Column system inner diameters may range from 1.0 millimeters (mm) to 10.0 mm, however these ranges certainly pose no restriction but do show the advantages that the apparatus can bring to the industry.

As such, it is an object of the present invention to provide an universal self-adjusting high pressure liquid connector designed for fluid transfer applications capable of self-adjusting, hand tight connection thereby eliminating the potential for improper connections due to variance in mating fitting geometry.

Another object of the present invention is to provide an apparatus that lends itself to both high and low pressure applications, i.e. those applications involving pressures both above and below 6000 psi.

It is further an object of the present invention to provide an apparatus which is chemically inert.

These and other objects of the present invention will become more readily apparent from the detailed description given hereafter. However, it should be understood that a detailed description and specific examples, while indicating preferred embodiments of the invention, are given by way of illustration only, since various changes and modifications within the spirit and scope of the invention will become apparent to those skilled in the art from this description.

BRIEF DESCRIPTION OF THE DRAWINGS

The invention can be more fully understood from the following detailed description thereof in connection with accompanying drawings described as follows:

FIG. 1 is a plan view of the universal self-adjusting high pressure liquid connector of the present invention depicted in a fully assembled condition;

FIG. 2 is sectional view taken through a vertical centerline of the FIG. 1 depiction;

FIG. 10 depicts a single-ended universal self-adjusting high pressure liquid connector further comprising an opposing fixed connector wherein the capillary tube is configured in a U-shape; and FIG. 11 is an exploded view of FIG. 10.

DETAILED DESCRIPTION OF THE PREFERRED EMBODIMENT

Figure 3:
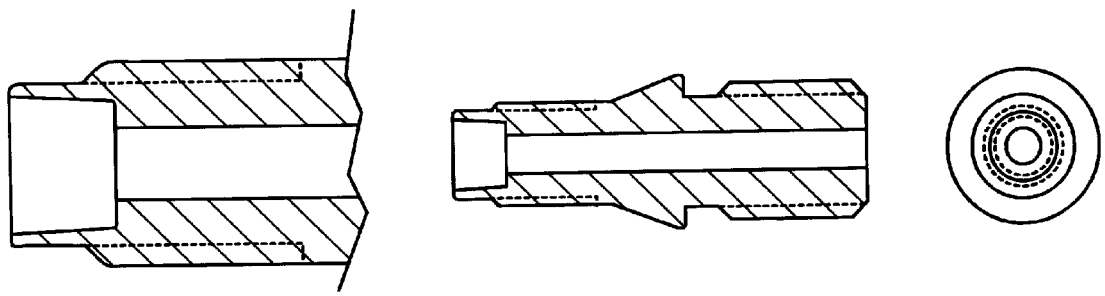
FIG. 3 is a sectional view of the stem portion of the FIG. 1 invention.

Throughout the following detailed description, in the event that similar reference characters are called out, they refer to similar elements in all figures capillary of the drawings.

Referring to FIGS. 1 and 2, there is depicted an apparatus for use as an end cap in a chromatography column or as a means of connecting two similar or dissimilar fittings. As FIG. 2 depicts, the assembly comprises a body 1, a stem 2, a removable ferrule 3, a fixed ferrule 4, a capillary tube 5, and a biasing spring 6. A label 7 is shown which incorporates a manufacturer's logo, but certainly is not necessary to the function of the invention.

In essence, the universal self-adjusting high pressure liquid connector of the present invention is constructed in the following manner: a spring 6 is slid or otherwise engaged onto the capillary tubing 5 and the fixed ferrule 4 is swaged or otherwise fixedly attached to the capillary tubing 5 at some predetermined position. The spring 6 is allowed to float upon the capillary tubing 5, i.e. slide freely along the capillary tubing 5 whereas the fixed ferrule 4 is secured in a predetermined position upon the capillary tubing 5. The spring 6 position on the capillary tubing 4 is a function of the apparatus's use and is made to accommodate the maximum and minimum capillary tubing 5 exposure necessary for the capillary tubing 5 to bottom out against the end of a column. The primary purpose of the fixed ferrule 4 is to provide a stationary location for the spring to act upon against the body 1 as the universal high pressure liquid connector self-adjusts to the interfaced column fitting. The predetermined position can be changed based upon the use of the invention but the manufacturer's preferred position for the fixed ferrule 4 accommodates all known liquid chromatography columns thus making the apparatus universal to all manufacturers.

It is important to note that the capillary tube 5 may vary in length and inside diameter without departing from the scope of the invention. It is this feature, in conjunction with the self-adjusting features of the present invention that makes the apparatus of the present invention truly universal.

The capillary tubing 5, the fixed ferrule 4 and the spring 6 are engaged within the body 1 of the universal high pressure liquid connector of the present invention. The stem 2 and the replaceable ferrule 3 comprises the remainder of the universal high pressure liquid connector that provides a leak free interface between the connector and column fittings.

Figure 4:
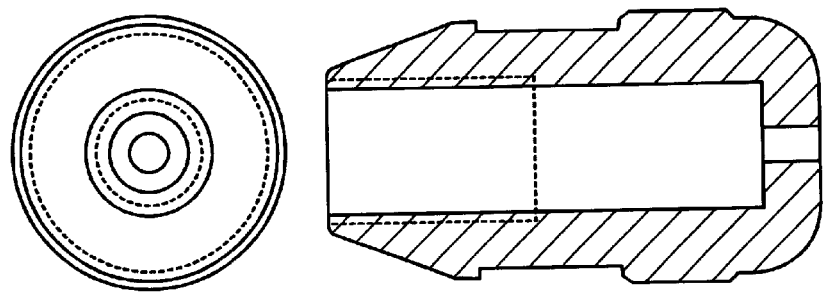
FIG. 4. is a sectional view of the body portion of the FIG. 1 invention.

The FIGS. 3 and 4 detail the configuration of the stem 2 and the body 1 respectively. The interface between the stem 2 and the body 1 is preferably threaded but is not required to be so. That is, the stem 2 typically has threads located on its exterior surface for operably engaging with threads located on the interior surface of the body 1. Additionally, since it is preferred that the present invention be installed without tools, a knurled surface is also desirable upon the exterior surface body 1 for assisting hand-tightening of the liquid universal high pressure connector onto column fittings. Though facilitating hand-tightening of the present invention, this feature is not necessary to the function of the apparatus.

The stem 2 is preferably comprised of a material resistant to galling as discussed in the above Summary to allow repeated assembly/disassembly and tightening among other reasons. The ferrule 3, is made to seat within the stem 2 whereby one surface of the replaceable ferrule 3 as well as the stem 2 itself, engages with a proprietary column fitting, thereby forming a leak free coupling without the use of tools. The replaceable ferrule 3 is replaceable and as such can be machined to have a v-groove in its outside diameter to enable easier extraction of the ferrule 3 from the stem 2.

Figure 5:
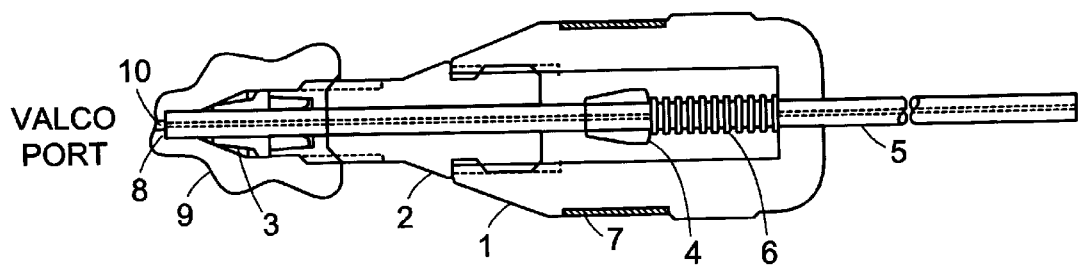
FIGS. 5 through 7 are sectional views of the FIG. 1 invention engaged with three distinct embodiments of chromatography columns symbolizing recognized industry standards and depicting the self-adjusting capabilities of the present invention.
Figure 6:
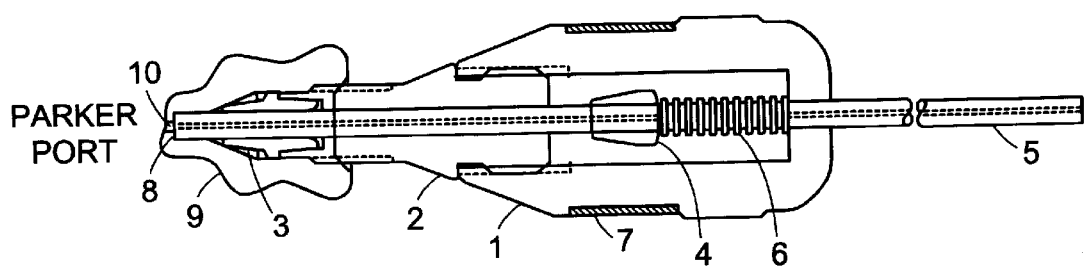
Figure 7:
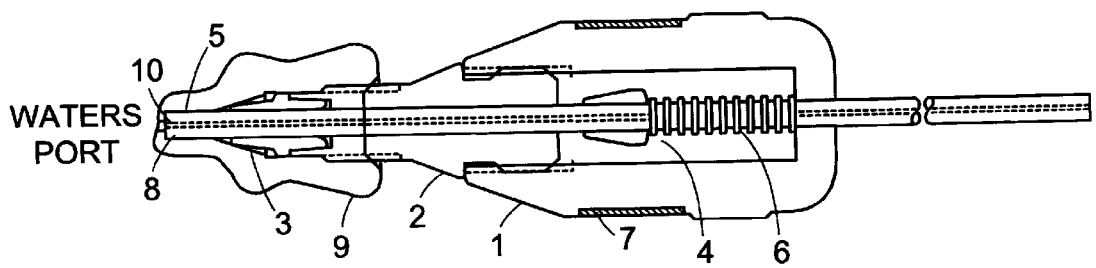

FIGS. 5 through 7 depict the universal high pressure liquid connector of the present invention engaged with various manufacturers' proprietary liquid chromatography columns. As can be seen by looking at each of FIGS. 5–7, the capillary tubing 5 bottoms out at the end of each proprietary HPLC column end fitting at point 8 thereby eliminating any potential for a dead volume. The capillary tubing 5 slides through the universal high pressure liquid connector until it bottoms out at the point 8. The spring 6 biases the tubing 5 into the interfacing and mating proprietary HPLC column fitting by expanding/compressing between the body 1 and the fixed ferrule 4. As shown in FIGS. 5–7, the capillary tubing 5 self-adjusts and bottoms out in each HPLC column fitting 9 at an interface point 8 between the universal self-adjusting high pressure liquid connector capillary tubing 5 and the column fitting port 10.

Figure 8:
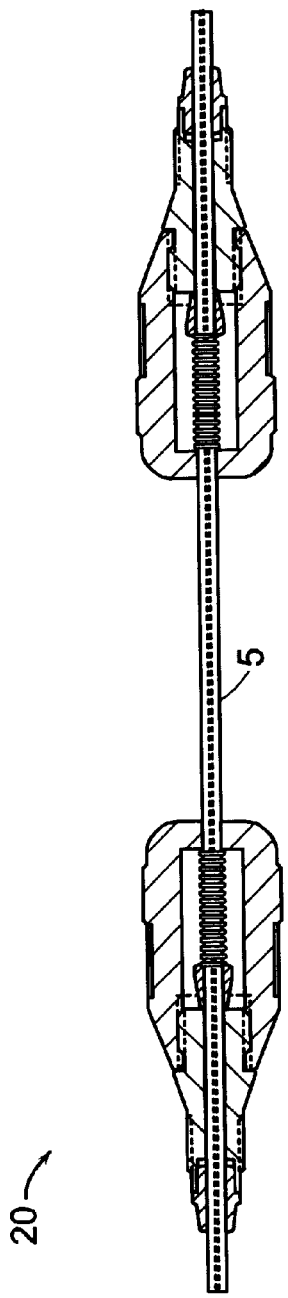
FIG. 8 depicts an double-ended embodiment of the present invention, showing two universal self-adjusting high pressure liquid connectors configured in a back-to-back relationship on a common capillary tube.
Figure 9:
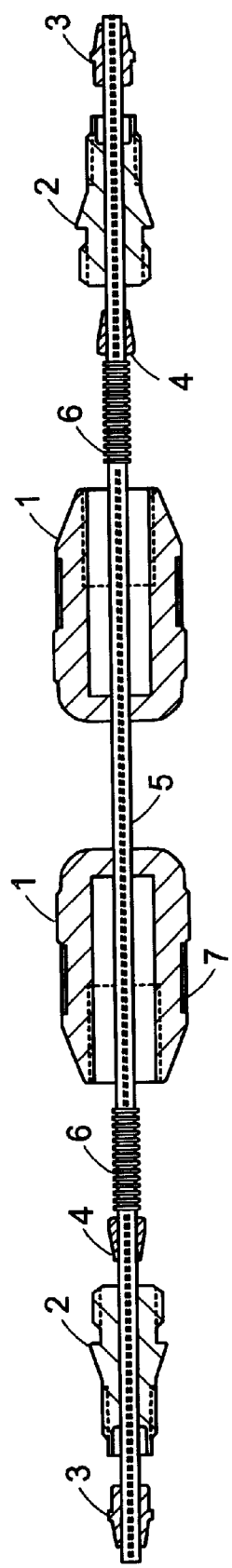
FIG. 9 is an exploded view of FIG. 8.

FIG. 8 depicts a double-ended embodiment of the present invention 20, showing two universal self-adjusting high pressure liquid connectors configured in a back-to-back relationship on a common capillary tube 5. Each of the two universal self-adjusting high pressure liquid connectors functions in a manner similar to the universal self-adjusting high pressure liquid connector described earlier. This embodiment is useful in situations where the need or desire exists to connect and disconnect two devices quickly, accurately and without leaks or dead volumes. The FIG. 9 is an exploded view of FIG. 8

FIG. 10 depicts a single-ended universal self-adjusting high pressure liquid connector 30 further comprising an opposing fixed depth connector 40 wherein the capillary tube 5 is configured in a U-shape. The universal high pressure liquid connector 50 is similar to the universal high pressure liquid connectors described earlier herein. The device 30 has a fixed depth connector 40 co-located on the capillary tubing 5 with the universal high pressure liquid connector 50. As shown in FIGS. 10 & 11, the fixed depth connector 40 could be composed of a compression screw 12 and a ferrule 10. The fixed depth connector 40 interfaces with HPLC column fittings of a specific port depth. Therefore, the ferrule 10 of the fixed depth connector 40 is swaged or otherwise fixedly attached to the capillary tubing 5. As shown in FIG. 10, the capillary tube 5 may be U-shaped. The U-shape of the capillary tube 5 accommodates closely spaced HPLC columns and fittings. FIG. 11 is an exploded view of FIG. 10.

The universal high pressure liquid connector of the present invention employs an internal biasing mechanism, preferably a spring 6 which applies force when the stem 2 is threaded or otherwise engaged with the female portion of a HPLC column end fitting. This operable engagement creates a positive seal between the capillary tubing 5 and the HPLC column end without the need for tools.

Other possible embodiments of the universal high pressure liquid connector could further comprise: 1) a ratcheting device where the tubing 5 extending from the replaceable ferrule 3 could be adjusted to accommodate different port depths; 2) providing a lever mechanism which could simultaneously force the capillary tubing 5 into both ends of a HPLC column at which time the body 1 would be hand tightened, thereby seating the ferrule 3; or 3) providing a spring attached to either the invention or a HPLC column which pulls the tubing into position within the column, thereby eliminating dead volume.

While the universal high pressure liquid connector has been described and illustrated with reference to a specific embodiment thereof, it is understood that other embodiments may be resorted to without departing from the present invention. Even in the embodiments disclosed herein, it should be noted that the capillary tube 5 may vary in length and inside diameter and outside diameter without departing from the scope of the invention. Therefore, the form of the invention set out above should be considered illustrative and not as limiting the scope of the following claims.

What is claimed is:

1. A universal self-adjusting high pressure liquid connector for use in high pressure liquid chromatography (HPLC) comprising:

a body, having a longitudinal bore therethrough, wherein the bore through said body is coincident with longitudinal axis of said body and extends the entire length of said body;

a stem having a longitudinal bore therethrough and a first end and a second end, the first end of said stem at least partally disposed within the longitudinal bore of said body, wherein the bore through said stem is coincident with the longitudinal axis of said body, extends the entire length of said stem and said stem is further sized to fit the longitudinal bore of said body;

an elongate capillary tube disposed within and extending through said stem and said body, said capillary tube having an outer diameter sized to fit snugly yet slidingly within the longitudinal bore of said stem and an inner diameter of a predetermined size;

a fixed ferrule fixedly attached to said capillary tube at a predetermined position on said capillary tube whereby said fixed ferrule is located between the first end of said stem disposed at least partially within said body and said body longitudinal bore;

a bias spring slidingly engaged about said capillary tube within the longitudinal bore of said body between said fixed ferrule and said body within the longitudinal bore of said body whereby engaging end of said stem with an HPLC fitting creates a leakproof seal connection and said spring adjusts and constantly biases said stem in sealed mating relationship with the HPLC fitting, thereby eliminating the potential for a dead volume; and an opposing fixed depth connector, located on said capillary tube, wherein said capillary tube is configured in a U-shape.

2. The self-adjusting high pressure liquid connector of claim 1 wherein said stem and said body are threadedly engaged one with the other, wherein the first end of said stem is threadedly engaged with said body.

3. The self-adjusting high pressure liquid connector of claim 1 wherein said connector is operably engageable with a HPLC fitting without the use of tools.

4. The self-adjusting high pressure liquid connector of claim 1 wherein at least a portion of an exterior surface of said body is knurled to facilitate the handling of said connector during the engagment of said connector with a HPLC fitting.

5. The self-adjusting high pressure liquid connector of claim 1 wherein said capillary tube may vary in length and inner diameter, and outer diameter.

6. The self-adjusting high pressure liquid connector of claim 1 wherein at least a portion of an exterior surface of said stem is threaded for threaded engagement with a threaded HPLC fitting.

7. The self-adjusting high pressure liquid connector of claim 6 wherein the exterior threads located on the exterior of said stem are located substantially near the second end of said stem.

8. The self-adjusting high pressure liquid connector of claim 6 wherein said the exterior threads located on said stem comprises material having anti-gall metallurgic properties.

9. The self-adjusting high pressure liquid connector of claim 6 wherein said the exterior threads located on said stem comprises NITRONIC-60 material.

10. The self-adjusting high pressure liquid connector of claim 6 wherein said the exterior threads located on said stem comprises GALL-TOUGH material.

11. The universal self-adjusting high pressure liquid connector of claim 1 further comprising a replaceable ferrule slidingly engaged on said capillary tube and seated in intimate contact with the second end of said stem for further ensuring a leakproof connection between the universal self-adjusting high pressure liquid connector and a HPLC fitting when operably engaged.

12. The self-adjusting high pressure liquid connector of claim 11 wherein said replaceable ferrule further comprises a v-shaped groove disposed longitudinally along the outside surface of said ferrule for easier extraction of said ferrule from said insert.

* * * * *